United States Patent
Barty

(10) Patent No.: US 11,357,458 B2
(45) Date of Patent: Jun. 14, 2022

(54) HIGH-CONTRAST, CONVERGENT X-RAY IMAGING WITH LASER-COMPTON SOURCES

(71) Applicant: Lawrence Livermore National Security, LLC, Livermore, CA (US)

(72) Inventor: Christopher P. J. Barty, Irvine, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 39 days.

(21) Appl. No.: 16/635,128

(22) PCT Filed: Jul. 23, 2018

(86) PCT No.: PCT/US2018/043342
§ 371 (c)(1),
(2) Date: Jan. 29, 2020

(87) PCT Pub. No.: WO2019/027712
PCT Pub. Date: Feb. 7, 2019

(65) Prior Publication Data
US 2020/0261042 A1   Aug. 20, 2020

Related U.S. Application Data

(60) Provisional application No. 62/539,452, filed on Jul. 31, 2017.

(51) Int. Cl.
*A61B 6/06* (2006.01)
*A61B 6/00* (2006.01)

(52) U.S. Cl.
CPC .............. *A61B 6/4085* (2013.01); *A61B 6/06* (2013.01); *A61B 6/4035* (2013.01);
(Continued)

(58) Field of Classification Search
CPC ....... A61B 6/4258; A61B 18/20; A61B 6/482; A61B 6/483; A61B 6/484; A61B 6/06
See application file for complete search history.

(56) References Cited

U.S. PATENT DOCUMENTS 5,864,597 A    1/1999  Kobayashi
7,742,574 B2 * 6/2010  Karlsson ................ G21K 1/06
                                               378/145
(Continued)

FOREIGN PATENT DOCUMENTS

WO    2015171923 A1   11/2015

OTHER PUBLICATIONS

International Search Report and Written Opinion for PCT/US2018/043342 corresponding to U.S. Appl. No. 16/635,128, 14 pages.
(Continued)

*Primary Examiner* — David P Porta
*Assistant Examiner* — Fani Boosais
(74) *Attorney, Agent, or Firm* — Ladas & Parry, LLP

(57) ABSTRACT

Techniques are provided for the production of high-contrast, x-ray and/or gamma-ray radiographic images. The images have minimal contributions from object-dependent background radiation. The invention utilizes the low divergence, quasi-monoenergetic, x-ray or gamma-ray output from a laser-Compton source in combination with x-ray optical technologies to produce a converging x-ray or gamma-ray beam with which to produce a high-contrast, shadowgraph of a specific object. The object to be imaged is placed within the path of the converging beam between the x-ray optical assembly and the focus of the x-ray beam produced by that assembly. The beam is then passed through an optically thick pinhole located at the focus of the beam. Downstream of the pinhole, the inverted shadowgraph of the object is then recorded by an appropriate 2D detector array.

60 Claims, 6 Drawing Sheets

(52) U.S. Cl.
CPC ............ *A61B 6/4258* (2013.01); *A61B 6/483* (2013.01); *A61B 6/484* (2013.01); *A61B 6/5205* (2013.01)

(56) References Cited

U.S. PATENT DOCUMENTS

| | | | |
|---|---|---|---|
| 9,364,191 B2* | 6/2016 | Ning | G01N 23/20091 |
| 9,412,481 B1 | 8/2016 | Fuller | |
| 9,632,039 B2* | 4/2017 | Den Boef | G03F 7/70641 |
| 10,349,908 B2* | 7/2019 | Yun | A61B 6/484 |
| 10,401,309 B2* | 9/2019 | Yun | A61B 6/484 |
| 10,459,347 B2* | 10/2019 | Boonzajer Flaes | G01N 21/956 |
| 10,757,795 B2* | 8/2020 | Miller | A61B 6/032 |
| 2002/0159561 A1 | 10/2002 | Cederstrom | |
| 2007/0121784 A1 | 5/2007 | Cederstrom | |
| 2008/0095312 A1 | 4/2008 | Rodenburg et al. | |
| 2009/0238339 A1 | 9/2009 | Carroll | |
| 2009/0266992 A1 | 10/2009 | Beekman | |
| 2016/0061750 A1 | 3/2016 | Den Boef | |

OTHER PUBLICATIONS

Extended European Search Report from European Patent Application No. 18841917.0 dated Mar. 25, 2021.

Dorthe Wildenschiel, et al., "X-ray imaging and analysis techniques for quantifying pore-scale structure and processes in subsurface porous medium systems", Advance in Water Resources, Jul. 1, 2012 (Jul. 1, 2012), XP055053878, ISSN: 0309-1708, DOI: 10.1016/j.advwatres.2012.07.018.

PCT International Preliminary Report on Patentability (Chapter II) with Written Opinion from PCT/US2018/043342 dated Sep. 25, 2019.

* cited by examiner

HIGH-CONTRAST, CONVERGENT X-RAY IMAGING WITH LASER-COMPTON SOURCES

CROSS-REFERENCE TO RELATED APPLICATIONS

This application claims the benefit of U.S. Provisional Patent Application No. 62/539,452 titled "High-Contrast, Convergent X-Ray Imaging with Laser-Compton Sources," filed Jul. 31, 2017, incorporated herein by reference.

STATEMENT AS TO RIGHTS TO INVENTIONS MADE UNDER FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC, for the operation of Lawrence Livermore National Laboratory.

BACKGROUND

Field

The present technology relates to x-ray imaging, and more specifically, it relates to techniques for producing high-contrast, x-ray and/or gamma-ray radiographic images having minimal contributions from object-dependent background radiation.

Description of Other Art

In conventional x-ray radiography, a shadowgraph of a desired object is created by placing the object to be imaged between a quasi-point source of x-rays and a 2-dimensional detector system, e.g., an x-ray film, an x-ray CCD camera, a scintillator or a camera. FIG. 1 illustrates conventional point projection X-ray imaging with a rotating anode bremsstrahlung source. The resolution of the radiograph, is set by the spatial extent of the x-ray source and the geometrical magnification of the arrangement. Since the first discovery of x-rays by Wilhelm Roentgen in 1896, medical x-ray imaging has been conducted in this manner. In Roentgen's case, the x-ray source was based on bremsstrahlung radiation produced by an energetic electron beam 10 impinging upon a metal target 12. Bremsstrahlung sources produce polychromatic x-rays into all directions. In practical applications, the source emission, is limited to a cone of radiation by placement of metal baffles/collimators 14 around the x-ray tube. Radiographs/shadowgraphs are created by ballistic x-rays with sufficient energy to penetrate the object 16. Constituents, e.g., features 18, within the object that have higher attenuation form dark regions on the detector 20. Low energy x-rays that are not of sufficient energy to penetrate the object are absorbed by the object and in medical applications form the majority of the unwanted dose received by the patient. Not all photons with sufficient energy to penetrate the object travel a ballistic path and contribute to the image 22. In fact, in medical procedures, the majority of photons incident at the detector plane (sometimes greater than 90%) are photons whose paths have been modified by Compton scattering within the object. These scattered photons when incident upon the detector reduce the contrast and resolution of the image, i.e., they blur the image.

Various schemes have been developed by the medical community with which to mitigate image degradation due to scattered radiation, the most common of which are angled grid plates of high atomic weight material, e.g., lead, placed in close proximity to the detector system. The angle of the grid materials is set to match the natural divergence of the bremsstrahlung source, i.e., to be parallel to the path of ballistic photons traveling from the source to the detector. This method while somewhat effective in reducing blur due to scattered radiation, also reduces the number of ballistic photons arriving at the detector, limits resolution, increases the dose required for the image, and adds to the complexity of the overall imaging system.

In other x-ray imaging applications, the object to be imaged by an external x-ray source may also produce radiation that impinges upon the detector system which then reduces the contrast and quality of the image. One example is the imaging of shocked materials that have been illuminated by high-energy lasers. The laser-irradiated material in this case can produce high-energy electrons that in turn produce thermal and line x-ray radiation within the object. This object-generated source of background x-ray radiation will also be incident upon the detector system along with any ballistic x-rays from the backlighting source. To create a useful image, the radiographic x-ray source must have sufficient flux to overcome this natural background. Similar issues can arise when imaging strongly radioactive materials such as spent nuclear fuel assemblies. FIG. 2 illustrates conventional point projection X ray imaging of a radiating object or object producing X-ray scatter 24. Note the difference between the recorded image 26 of FIG. 2 and the recorded imaged 22 of FIG. 1. Common elements in FIGS. 1 and 2 are labeled with the same reference numbers.

SUMMARY

Disclosed herein is high-contrast, convergent x-ray imaging with laser-compton sources. The present technology includes a method by which high-contrast, x-ray and/or gamma-ray radiographic images may be produced with minimal contributions from object-dependent background radiation. The technology utilizes the low divergence, quasi-monoenergetic, x-ray or gamma-ray output from a laser-Compton source in combination with x-ray optical technologies to produce a converging x-ray or gamma-ray beam with which to produce a high-contrast, shadowgraph of a specific object. The object to be imaged is placed within the path of the converging beam between the x-ray optical assembly and the focus of the x-ray beam produced by that assembly. The beam is then passed through an optically thick pinhole located at the focus of the beam. The diameter in this pinhole is designed to be of order that of the x-ray or gamma-ray focal spot. In this way, all scattered radiation and/or self-emission from the object that does not pass through the pinhole is rejected and does not impinge upon the detector system. Downstream of the pinhole, the inverted shadowgraph of the object is then recorded by an appropriate 2D detector array. Depending upon the specifics of the geometry, the magnitude of background radiation arriving at the detector system from this invention may be reduced by many orders of magnitude relative to that of conventional x-ray point projection imaging. It should be noted that a prerequisite for this architecture is an x-ray or gamma-ray source that is compatible with existing x-ray optics which in general require quasi-collimated and quasi-monoenergetic input to perform optimally.

Applications of this invention include but are not limited to radiography of objects with significant self-emission, e.g., laser-plasmas, radioactive materials, line emission from x-ray or gamma-ray excited constituents within the object etc., as well as objects for which x-ray or gamma-ray illumination produces significant scattered radiation, e.g., medical radiography, industrial radiography etc.

DETAILED DESCRIPTION

Figure 1:
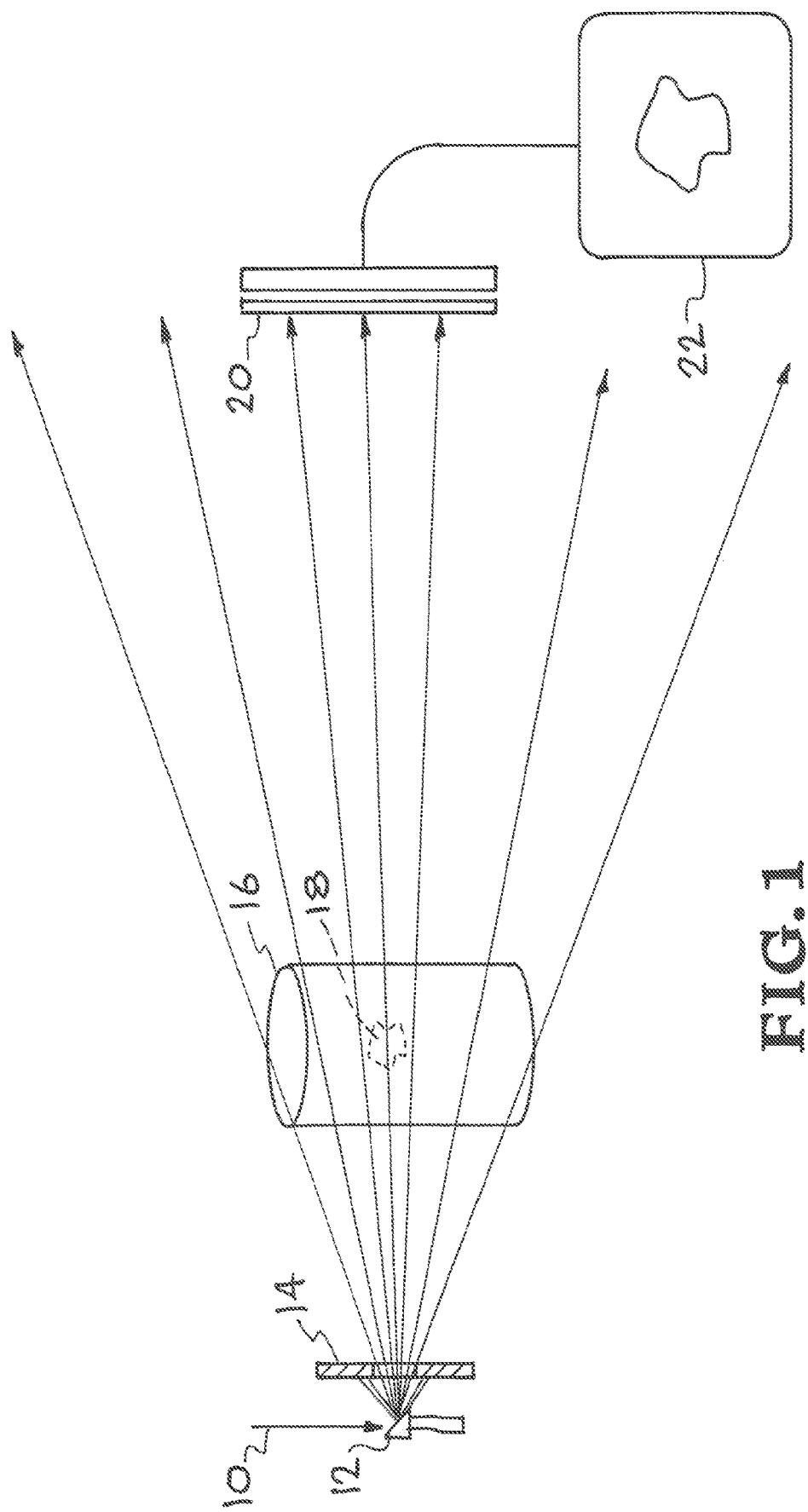
FIG. 1 illustrates conventional point projection X-ray imaging with a rotating anode Bremsstrahlung source.
Figure 2:
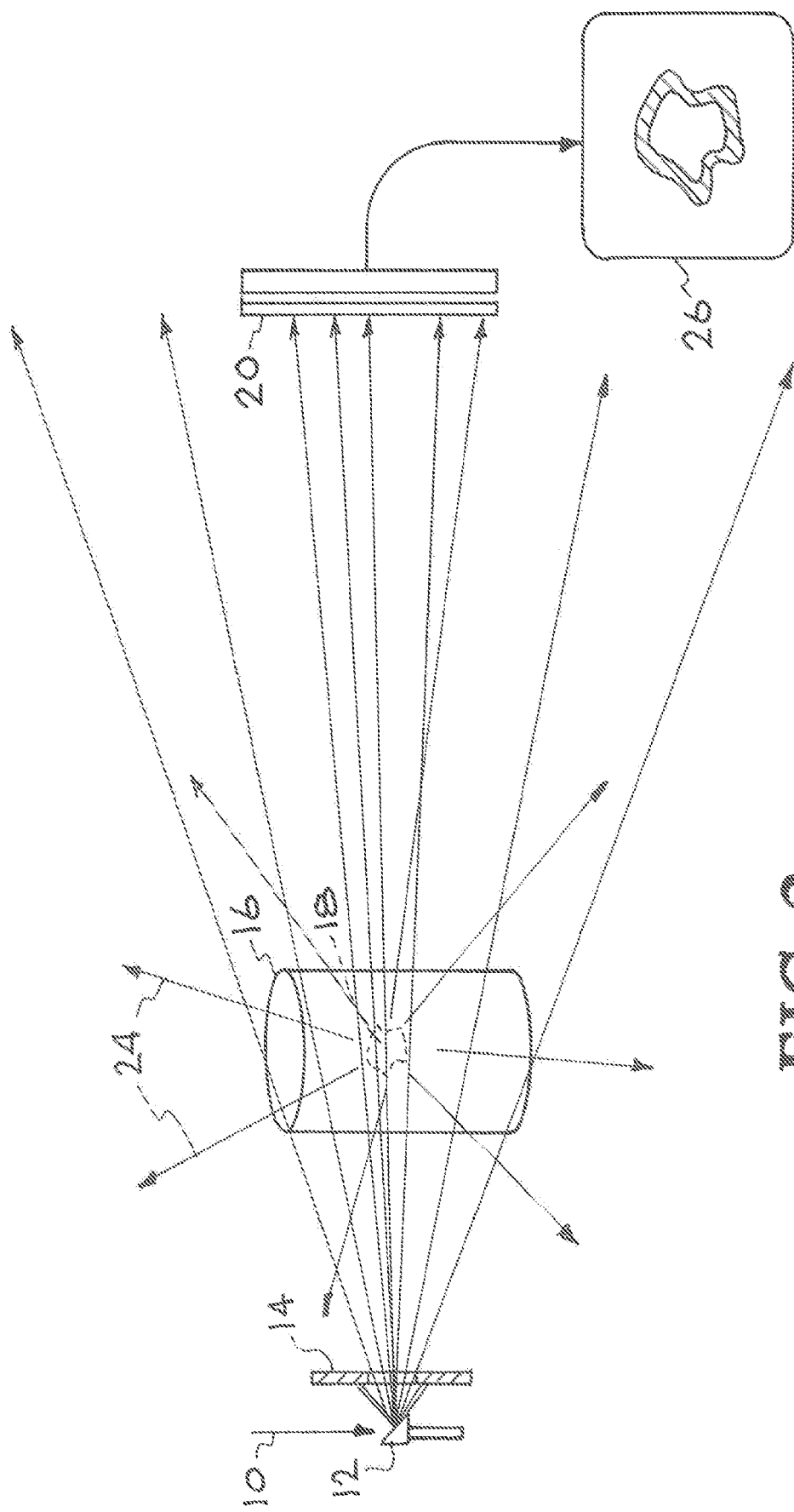
FIG. 2 illustrates conventional point projection X ray imaging of a radiating object or object producing X-ray scatter.
Figure 3:
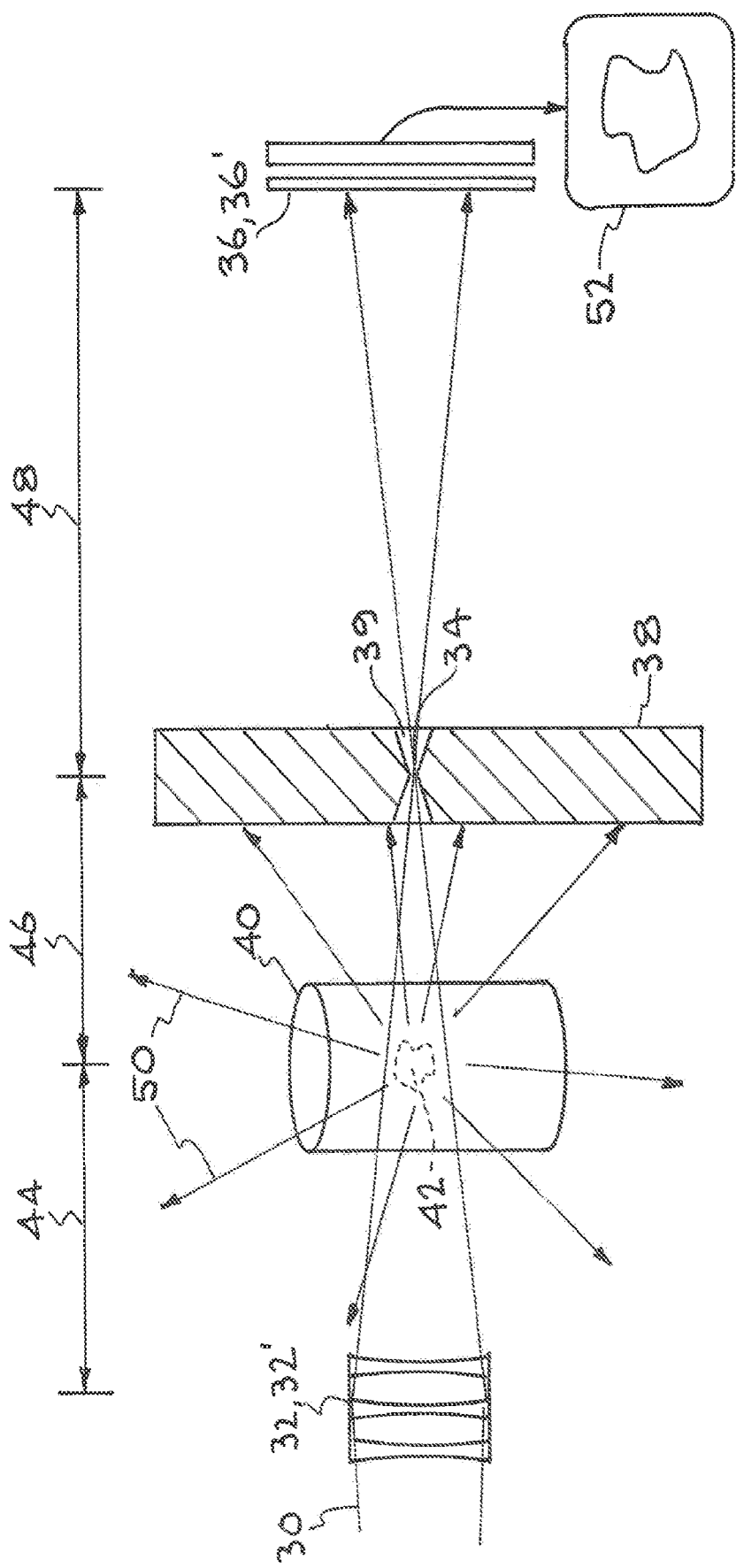
FIG. 3 shows convergent imaging of an object whose spatial extent is small compared to the transverse dimension of the convergent x-ray beam.
Figure 4:
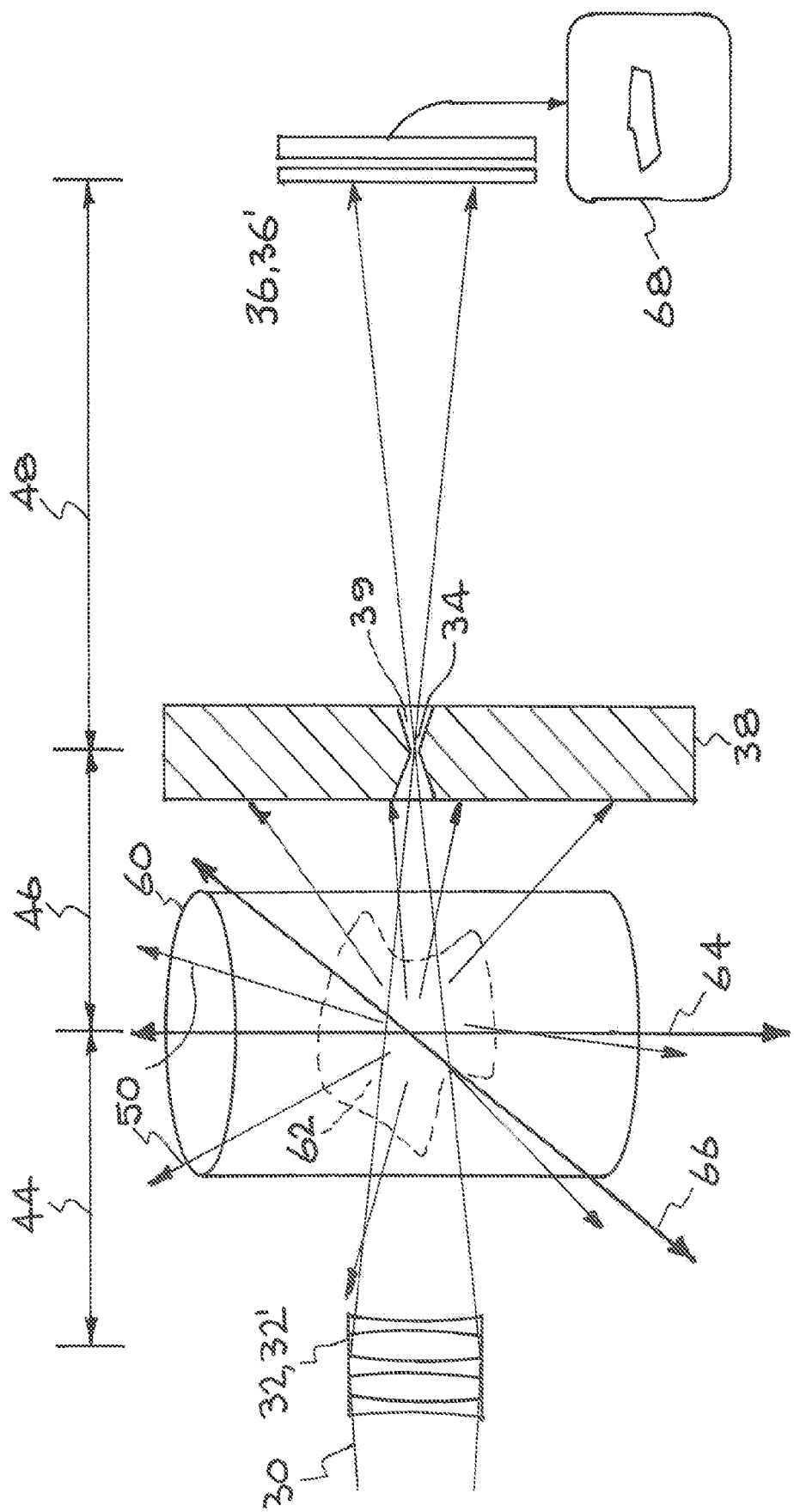
FIG. 4 illustrates convergent imaging of a large object where a full 2D image is obtained by scanning the object relative to the x-ray beam axis.

In the present technology, the output beam from a laser-Compton x-ray source is manipulated with x-ray optics to form a focus at a fixed distance from the laser-electron interaction point at which the laser-Compton x-rays are produced. The object to be imaged is placed between the laser-electron interaction point and the laser-Compton beam focus formed by the x-ray optics. A pinhole is placed at the point of the laser-Compton beam focus. FIG. 3 shows convergent imaging of an object whose spatial extent is small compared to the transverse dimension of the convergent x-ray beam. The pinhole is constructed from highly attenuating materials and is configured to have sufficient thickness so as to block any x-ray radiation not passing through the pinhole. The laser-Compton x-ray radiation that passes through the pinhole is collected by a conventional, 2-dimensional, x-ray detector system, e.g., x-ray film, an x-ray CCD. There are two imaging configurations for this arrangement. In the first, the object is small compared to the beam diameter at the location at which it is placed. In this case an inverted shadowgraph of the full object is created at the detector array shown in FIG. 3. In the second, the object is large compared to the laser-Compton beam diameter at the location at which it is placed. In this case, a complete image of the object is obtained by scanning the entire object and beam relative to each other with the beam direction and pinhole location fixed with respect to one another. FIG. 4 illustrates convergent imaging of a large object where a full 2D image is obtained by scanning the object relative to the x-ray beam axis. In both cases, scattered radiation and/or self-emission from the object are blocked from reaching the detector array and a high-quality, high-contrast radiograph is produced.

More specifically, the exemplary embodiment of FIG. 3 shows a quasi-mono-energetic, laser Compton x-ray beam 30 focused by a compound refractive x-ray lens 32 to a focal point 34. The beam 30 propagates through focal point 34 to the detector 36. Element 38 comprises a pinhole 39 co-located with focal point 34. The material and thickness of element 38 must be sufficient to prevent passage of the beam except through the pinhole aperture. In one embodiment, the element is made of lead, or other highly attenuating material and has a thickness of greater than 10 micrometers. An object 40 is placed between the lens 32 and the focal point 34 of beam 30. This figure shows a feature 42 within object 40. Feature 42 is small compared to the transverse dimension of beam 30, i.e., the beam entirely covers feature 42. The figure shows a distance 44 from lens to object, a distance 46 from object to pinhole and a distance 48 that has been set for a desired magnification. X-ray self-emission/x-ray scatter 50 are produced when the beam propagates through the object. Only the portion of scatter 50 that passes through the pinhole will propagate onto the detector. This system produces a high contrast recorded image 52.

The exemplary embodiment of FIG. 4 can be utilized when the feature to be imaged is large relative to the transverse dimension of the x-ray beam. Certain elements of this embodiment can be identical to those of FIG. 3, and like references numbers are used for those elements, however, this embodiment includes an object 60 with a feature 62 that is larger than the transverse dimension of the beam 30. To obtain an image of the entire feature 62, the object can be scanned (moved) relative to the x-ray beam. A complete image of the object is obtained by scanning the entire object and beam relative to each other with the beam direction and pinhole location fixed with respect to one another. The arrow 64 signifies movement of the object in one direction relative to the beam and the arrow 66 signifies movement in the orthogonal direction to that of arrow 64. The image 68 is recoded at one position in the x-y scan of the object relative to the x-ray beam axis.

This invention relies on the physical properties of laser-Compton x-ray sources and on x-ray optical systems matched to these sources. Laser-Compton scattering (sometimes confusingly referred to as inverse Compton scattering) is the process in which an energetic laser pulse is scattered off of a short duration, bunch of relativistic electrons. This process has been recognized as a convenient method for production of short duration bursts of quasi-mono-energetic, x-ray radiation. When interacting with the electrons, the incident laser light induces a transverse motion on the electrons. The radiation from this motion when observed in the rest frame of the laboratory appears to be a forwardly directed, Doppler upshifted beam of high-energy photons. For head on collisions, the full spectrum of the laser-Compton source extends from zero to four times gamma squared times the energy of the incident laser, where gamma is the normalized energy of the electron beam, i.e., gamma=1 when electron energy=511 keV. The highest energy of the laser-Compton source may be tuned, by changing the energy of the electron bunch and/or the energy of the laser photons. Beams of high-energy radiation ranging from few keV to >MeV have been produced by this process and used for a wide range of applications.

Figure 5:
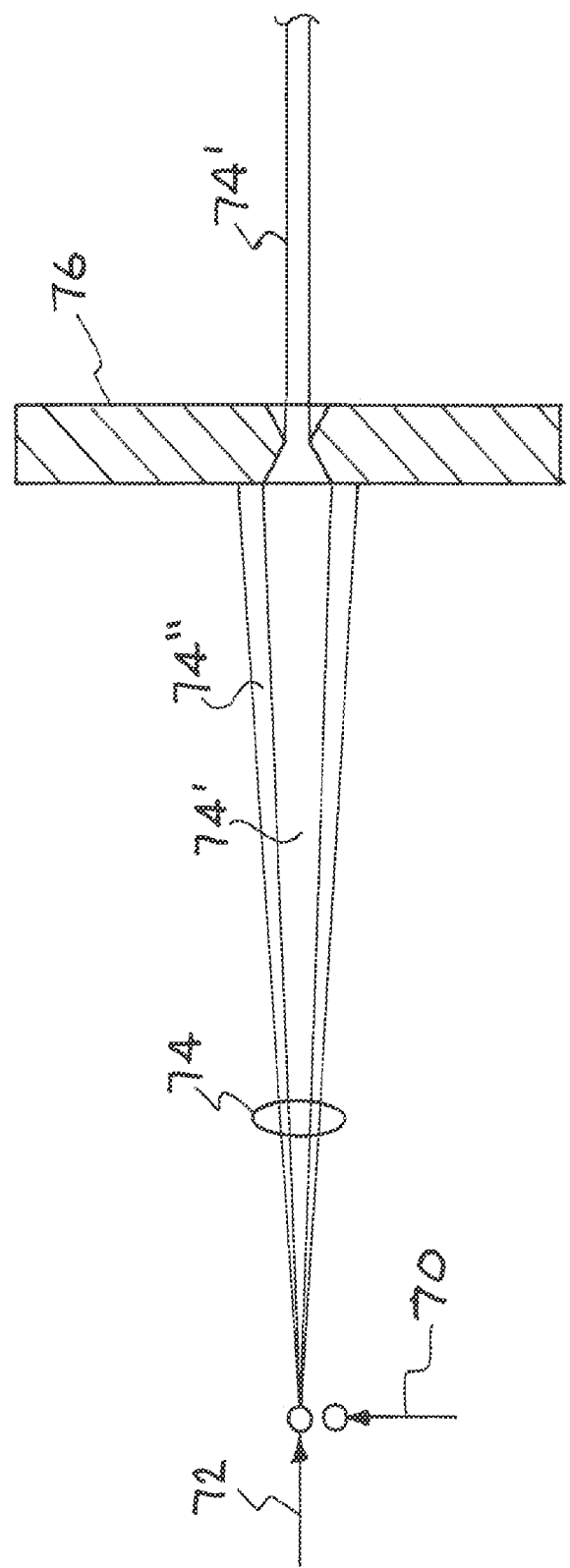
FIG. 5 illustrates an angle correlated laser Compton spectrum.

The spectrum of the radiated laser-Compton light is highly angle-correlated about the propagation direction of the electron beam with highest energy photons emitted only in the forward direction and the angle of lower energy photons relative to the propagation axis determined by the conservation of energy and momentum. FIG. 5 illustrates an angle correlated laser-Compton spectrum. Photons from an energetic laser pulse 70 collide with relativistic electrons 72 to produce laser-Compton emission beam 74. In the transverse dimension of the beam 74, the highest energy laser-Compton photons are located in the central part 74' of the beam and the lower energy laser-Compton photons are located on the outer part 74" of the beam. The photon energy of the beam can be characterized as a continuum where the highest energy photons are along the central axis of the beam and the photon energy falls off with distance orthogonal to the central axis. With an appropriately designed aperture, such as aperture 76, placed in the path of the laser-Compton beam, one may create a quasi-mono-energetic x-ray or gamma-ray beam whose bandwidth ($\Delta E/E$) is 10%. Simulations indicate that on-axis bandwidths of order 0.1% can be obtained from properly designed laser-Compton systems.

The output radiation from Laser-Compton x-ray sources is also highly collimated especially in comparison with that from conventional, bremsstrahlung, rotating-anode x-ray sources. The cone angle of emission for the half-bandwidth spectrum of a laser-Compton source is approximately 1 on gamma which is typically a few milli-radians or less. The cone angle for narrowest bandwidth, on-axis portion of the spectrum may be of order 10's of micro-radians for appropriately designed systems. Typical rotating anode sources have beam divergences set by collimators of ~500 milli-radians.

The high degree of collimation and quasi-mono-energetic character of laser-Compton x-ray sources is enabling to beam manipulation with a variety of x-ray optical technologies including but not limited to: compound refractive optics, capillary x-ray optics, x-ray zone plates, grazing incidence metal x-ray optics and grazing incidence multi-layer-coated x-ray optics. The exact choice of optic will depend upon the energy of the x-rays desired for a particular imaging task. For the sake of providing an example, we will consider a laser-Compton beam with peak, on-axis, x-ray energy of 100 keV that is manipulated for convergent imaging and noise reduction by a compound refractive x-ray optic.

Figure 6:
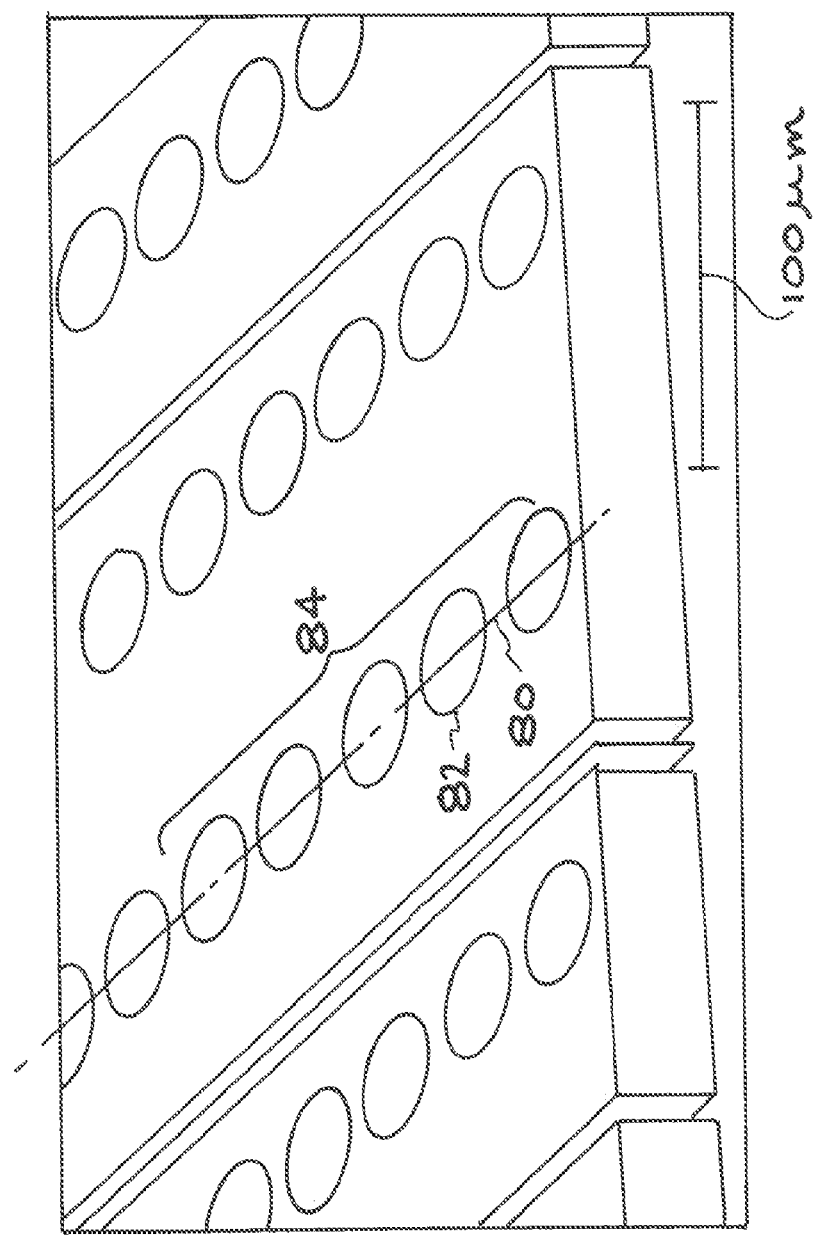
FIG. 6 is an image of compound refractive x-ray optics produced by lithography in Silicon.

In the x-ray region of the electro-magnetic spectrum, the index of refraction of all materials is less than unity and differs from unity by only a small amount. For this reason, positive, refractive x-ray lenses have the shape of negative lenses in the visible portion of the spectrum, i.e., they are thinnest on axis and become thicker as one moves away from the optical axis. Because the index of materials is close to unity in the x-ray regime, a single x-ray refractive optic with a diameter matched to that of the laser-Compton beam would have very little optical power and thus very little influence on the natural divergence of the laser-Compton x-ray beam. See FIG. 6. Compound refractive x-ray optics, however, produce optical power by passing the x-ray beam along an optical axis (e.g., See FIG. 6, optical axis 80) through a series of refractive elements (e.g., See FIG. 6, single lens 82 and series of lenses 84). The sum of many weak lenses can produce sufficient optical power to collimate and/or focus a laser-Compton x-ray beam. Compound refractive x-ray optics have been developed, demonstrated, and utilized with synchrotron light sources to manipulate quasi-mono-energetic, synchrotron x-ray beams. Compound x-ray optics may be formed lithographically in solid wafer materials such as silicon or may be created by the stacking of coined metal discs each of which having a roughly parabolic shape. FIG. 6 is an image of compound refractive x-ray optics produced by lithography in Silicon. In the lithographic case, a one-dimensional focusing element is created in the material wafer and two-dimensional beam manipulation is produced by passing the full beam through two sets of optics oriented at 90 degrees with respect to one another. The quasi-mono-energetic nature of the laser-Compton source is well matched to compound optics whose transverse spatial profile is roughly parabolic.

For a given laser-Compton source with specific x-ray energy and source size, a compound x-ray refractive optic can be designed to either collimate the output and produce beams of a few 100 microns to a few millimeters in diameter or may be designed to focus the laser-Compton beam to a small spot. The size of the focal spot that can be produced will depend upon the focal length of the compound x-ray optic and the divergence properties of the laser-Compton x-ray beam that in turn depends upon the initial spot size of the laser and electron interaction of the laser-Compton source. Focused beams of a few microns are practical and focused beams of less than a micron are feasible.

As discussed above, the converging x-ray beam produced by the combination of an appropriate laser-Compton x-ray source and x-ray optic may be used to create high-contrast, "background-free" images of an object in two ways.

In the first instance, the object is small compared to the beam diameter at the location at which the object is placed. See FIG. 3. The shadow of the object is produced in the converging beam. This is opposite to the conventional situation in which the x-ray shadow is produced in the diverging beam emanating from a bremsstrahlung source. As illustrated in FIG. 3, an inverted shadow of the object is produced at the detector after the beam passes through its focus. Unwanted scatter or self-emission from the object is prevented from reaching the detector by placement of an optically thick pinhole at the position of the x-ray focus. The practical limitations of this mode of operation are the size of the x-ray optical assembly used to focus the laser-Compton beam and any spatial constraints that may exist due to the distance required for the laser-Compton beam to diverge to an appropriate size and distance required for the x-ray optic to focus the beam. Typically, these constraints limit the object size to millimeters or less. One practical medical application would be precision imaging of micron-scale capillary structures in angiographic procedures. The degree to which unwanted scatter from the object may be reduced from the image depends upon the distance from the object to the pinhole. For the example illustrated in FIG. 3, at least 10 orders of magnitude reduction in wide-angle background is achievable. Given that typical whole body medical imaging produces roughly 10 scattered photons for every ballistic, image-carrying photon, elimination of background in this manner can enable significant improvement in image quality and/or reduction in dose to the patient. It should be noted that this mode of imaging is not practical with conventional rotating anode-based bremsstrahlung x-ray sources as the natural divergence of the source severely limits the number of photons incident upon the x-ray optics and the wide bandwidth of the source would not be focused to a single spot due to chromatic variation of the refractive index within the compound refractive optic.

In the second mode of operation, the object is large compared to the beam diameter at the location at which the object is placed. See FIG. 4. The shadow of only a portion of the object is produced in the converging beam and thus the object and beam must be scanned relative to one another in order to produce a full image of the object. However, for each location within the scan, the same reduction in scattered radiation impinging upon the detector is achievable as in the previous example and again provides a significant improvement in signal to noise at the detector.

It should be noted that in both cases mentioned above, the laser-Compton beam is attenuated by absorption and scatter losses in the x-ray optic material. For some compound x-ray optics, these losses may be up to 90% of the incident beam flux. However, unlike the use of grid plates for scatter reduction in conventional imaging, this attenuation occurs before the object is illuminated and thus does not require increased exposure to the patient to improve image contrast. For a given number of desired ballistic, image-forming photons at the detector, the convergent imaging geometry of this invention will expose the patient to a lower dose and for a given signal to noise at the detector (where noise is dominated by scattered radiation), the required dose to the patient may be orders of magnitude lower.

It should be further noted that the principles described above are also true if the object produces self-emission at energies similar to the illuminating laser-Compton x-ray beam. The same configurations and techniques described in this invention can be used to block self-emission from the object from impinging upon the imaging detector. Precision imaging of radioactively hot materials, laser-excited materials etc., becomes viable with this invention.

The following are some exemplary variations of laser-Compton convergent imaging technique described above.

1. The laser-Compton beam is first collimated with an appropriate x-ray optic and then focused with a second optic through a background-removing pinhole. The object is placed in either the collimated beam, or the converging beam before the pinhole. Referring to FIGS. 3 and 4, compound refractive x-ray lens 32 can be replaced with a combination of optics 32' comprising (i) an x-ray optic or compound optics, configured to collimate beam 30 and (ii) an x-ray optic, or compound optics, configured to focus the collimated beam through the pinhole of element 38. In one alternate configuration, object 40 with feature 42 can be located between the collimating optic(s) and the focusing optic(s) of optics 32'.

2. The laser-Compton beam is tuned to just above specific inner-shell, ionization threshold of a particular atomic species within the object to enhance contrast in the image and/or enable elemental material identification within the object.

3. The laser-Compton beam is tuned to a nuclear resonance fluorescence transition to enhance contrast and/or enable isotopic material identification within the object.

4. The detector system is gated to be on only during the arrival of the ballistic image-forming photons further discriminating against background and scattered radiation. Accordingly, detector system 36 of FIGS. 3 and 4 can be replaced with a gated detector system 36'.

5. The x-ray optic 32 or 32' used to collimate and/or focus the laser-Compton beam is designed so as to have a spatially varying structure such that lower energy, higher angle, laser-Compton photons incident upon the optic are focused to the same spot and same spot size as higher energy, on axis, laser-Compton photons. That is, the chromatic aberrations of the optic are matched to the spectral-angle dependency of the laser-Compton source.

6. The pinhole element 38 used for rejection of background is composed of a thick plate of highly absorbing material into which a conical hole 39 is made that matches the convergence and/or divergence of the laser-Compton beam at and around the focus.

7. The laser-Compton beam is focused by optic 32 or 32' in only one dimension and allowed to diverge in accordance with the physics of the laser-Compton process in the other dimension. The pinhole 39 in this case is a slit matching the focal size of the beam in the focusing dimension. This mode enables line scanning of the object.

8. The laser-Compton beam is focused by two, one-dimensional, compound x-ray optics 32 or 32' oriented at 90 degrees with respect to one another and that focus to different locations. One of these is used to create a fan beam and the other to produce a line focus at which a slit is placed to reduce background radiation. This mode enables line scanning of the object.

9. The laser-Compton beam is shaped by lens 32 or 32' such that the beam is collimated in one dimension by a one-dimensional, compound x-ray optic and then focused in the other dimension by another one-dimensional x-ray optic oriented at 90 degrees with respect to the first. At the focus of the second optic, a slit is placed to reduce background radiation. This mode reduces the alignment issues of the background rejection device.

10. The laser-Compton beam in 7) is tuned as described in 2) or 3) to increase contrast and/or enable material identification within the object.

11. The laser-Compton beam in 8) is tuned as described in 2) or 3) to increase contrast and/or enable material identification within the object.

12. The laser-Compton beam in 9) is tuned as described in 2) or 3) to increase contrast and/or enable material identification within the object.

All elements, parts and steps described herein are preferably included. It is to be understood that any of these elements, parts and steps may be replaced by other elements, parts and steps or deleted altogether as will be obvious to those skilled in the art.

Broadly, this writing discloses at least the following: Techniques are provided for the production of high-contrast, x-ray and/or gamma-ray radiographic images. The images have minimal contributions from object-dependent background radiation. The invention utilizes the low divergence, quasi-monoenergetic, x-ray or gamma-ray output from a laser-Compton source in combination with x-ray optical technologies to produce a converging x-ray or gamma-ray beam with which to produce a high-contrast, shadowgraph of a specific object. The object to be imaged is placed within the path of the converging beam between the x-ray optical assembly and the focus of the x-ray beam produced by that assembly. The beam is then passed through an optically thick pinhole located at the focus of the beam. Downstream of the pinhole, the inverted shadowgraph of the object is then recorded by an appropriate 2D detector array.

Concepts:

This writing also presents at least the following concepts:

1. A method, comprising:

providing an x-ray or gamma-ray output beam;

directing said output beam through at least one x-ray and/or gamma-ray optic to produce a converging beam directed toward a focal point;

positioning an object within the path of said output beam or said converging beam to produce an altered beam;

providing an aperture having an opening located at the focal position of said altered beam, wherein at least a portion of said altered beam passes through said opening to produce a diverging beam; and detecting said diverging beam.

2. The method of concepts 1 and 3-32, wherein said output beam is a quasi-monoenergetic, x-ray or gamma-ray output beam provided from a laser-Compton source.

3. The method of concepts 1, 2 and 4-32, wherein said at least one x-ray and/or gamma-ray optic comprises at least one refractive x-ray lens.

4. The method of concepts 1-3 and 5-32, wherein said at least one x-ray and/or gamma-ray optic comprises at least one compound x-ray optic.

5. The method of concepts 1-4, 6 and 8-32 wherein said object is positioned within the path of said converging beam.

6. The method of concepts 1-5 and 8-32, wherein said at least one x-ray and/or gamma-ray optic comprises at least one collimating optic followed by at least one focusing optic, wherein said output beam is first collimated by said at least one collimating optic and then focused by said at least one focusing optic to produce said converging beam.

7. The method of concept 6, wherein said object is positioned between said at least one collimating optic and said at least one focusing optic.

8. The method of concepts 1-7 and 9-32, wherein said object comprises a feature of interest that is smaller than the transverse dimension of said converging beam such that said converging beam completely covers said feature of interest.

9. The method of concepts 1-8 and 14-32, wherein said object comprises a feature of interest that is larger than the transverse dimension of said converging beam such that said converging beam does not completely cover said feature of interest.

10. The method of concept 9, further comprising scanning said object relative to the position of said converging beam.

11. The method of concept 10, wherein the step of detecting said diverging beam comprises collecting a plurality of images of said diverging beam during the step of scanning said object.

12. The method of concept 11, wherein said plurality of images altogether provide a complete image of said feature of interest.

13. The method of concept 9, wherein a complete image of said feature of interest is obtained by scanning said object and beam relative to each other with the location of said converging beam and the location of said opening fixed with respect to one another.

14. The method of concepts 1-13 and 15-32, wherein said aperture comprises a material that is highly attenuating to x-rays or gamma rays.

15. The method of concepts 1-14 and 16-32 wherein said opening comprises a shape selected from the group consisting of a pinhole and a slit.

16. The method of concepts 1-15 and 18-32, wherein said opening comprises a conical hole.

17. The method of concept 16, wherein said cortical hole matches the convergence and/or divergence of the laser-Compton beam at and around the focus.

18. The method of concepts 1-17 and 19-32, wherein said opening comprises a diameter that is of the order of the x-ray or gamma-ray focal spot at said opening.

19. The method of concept 1-18 and 20-32, wherein all scattered radiation and/or self-emission from said object that does not pass through said opening is rejected and is not detected.

20. The method of concepts 1-19 and 21-32, wherein said aperture is constructed from highly attenuating materials and is configured to have sufficient thickness so as to block any x-rays or gamma rays not passing through said opening.

21. The method of concepts 1-20 and 22-32, wherein the step of detecting said diverging beam is carried out with a 2-dimensional, x-ray detector system.

22. The method of concepts 1-21 and 23-32, further comprising tuning said output beam to just above a specific inner-shell, ionization threshold of a particular atomic species within said object to enhance contrast in the image and/or enable elemental material identification within the object.

23. The method of concepts 1-22 and 24-32, further comprising tuning said output beam to a nuclear resonance fluorescence transition of a particular atomic species within said object to enhance contrast and/or enable isotopic material identification within said object.

24. The method of concepts 1-23 and 25-32, wherein the step of detecting said diverging beam is carried out with a gated detector system, the method further comprising gating said detector system so that it, is on only during the arrival of ballistic image-forming photons of said diverging beam, thereby further discriminating against background and scattered radiation.

25. The method of concept 2, wherein said at least one x-ray and/or gamma-ray optic comprises a spatially varying structure such that lower energy, higher angle, laser-Compton photons of said output beam that are incident upon said at least one x-ray and/or gamma-ray optic are focused to the same spot and same spot size as higher energy, on axis, laser-Compton photons of said output beam.

26. The method of concept 2, wherein chromatic aberrations of at least one x-ray and/or gamma-ray optic are matched to the spectral-angle dependency of said laser-Compton source.

27. The method of concept 2, wherein said at least one x-ray and/or gamma-ray optic directs said output beam to a focus at said focal point in only one dimension and allows said output beam to diverge in accordance with the physics of the laser-Compton process in the other dimension and wherein said opening is a slit matching the focal size of said output beam in the focusing dimension.

28. The method of concept 27, further comprising tuning said output beam to increase contrast and/or enable material identification within said object.

29. The method of concept 2, wherein said at least one x-ray and/or gamma-ray optic comprises two, one-dimensional, compound x-ray optics oriented at 90 degrees with respect to one another and that focus to different locations, wherein one of these a fan beam of one dimension of said output beam and the other produces a line focus of said output beam, wherein a slit is placed at said line focus to reduce background radiation.

30. The method of concept 29, further comprising tuning said output beam to increase contrast and/or enable material identification within said object.

31. The method of concept 2, wherein said at least one x-ray and/or gamma-ray optic comprises a first one-dimensional, compound x-ray optic and a second one-dimensional, compound x-ray optic oriented at 90 degrees with respect to said first one-dimensional, compound x-ray optic, wherein said the output beam is collimated in one dimension by said first one-dimensional, compound x-ray optic and then focused in the other dimension by said second one-dimensional x-ray optic, wherein a slit is placed at said focal point to reduce background radiation.

32. The method of concept 31, further comprising tuning said output beam to increase contrast and/or enable material identification within said object.

33. An apparatus, comprising:
a source for providing an x-ray or gamma-ray output beam;
at least one x-ray and/or gamma-ray optic to produce, from said output beam, a converging beam directed toward a focal point, wherein an object positioned within the path of said output beam or said converging beam will result in an altered beam;
an aperture having an opening located at the focal position of said altered beam, wherein at least a portion of said altered beam will pass through said opening to produce a diverging beam; and
a detector positioned for detecting said diverging beam.

34. The apparatus of concepts 33 and 35-56, wherein said source is a laser-Compton source and wherein said output beam is a quasi-monoenergetic, x-ray or gamma-ray output beam provided from said laser-Compton source.

35. The apparatus of concepts 33, 34 and 36-56, wherein said at least one x-ray and/or gamma-ray optic comprises at least one refractive x-ray lens.

36. The apparatus of concepts 33-35 and 37-56, wherein said at least one x-ray and/or gamma-ray optic comprises at least one compound x-ray optic.

37. The apparatus of concepts 33-36 and 38-56, wherein said at least one x-ray and/or gamma-ray optic comprises at least one collimating optic followed by at least one focusing optic, wherein said output beam will be first collimated by said at least one collimating optic and then focused by said at least one focusing optic to produce said converging beam.

38. The apparatus of concepts 33-37 and 39-56, further comprising means for scanning said object relative to the position of said converging beam.

39. The apparatus of concepts 33-38 and 40-56, wherein said aperture comprises a material that is highly attenuating to x-rays or gamma rays.

40. The apparatus of concept 33-39 and 41-56, wherein said opening comprises a shape selected from the group consisting of a pinhole and a slit.

41. The apparatus of concepts 33-40 and 43-56, wherein said opening comprises a conical hole.

42. The apparatus of concept 41, wherein said conical hole matches the convergence and/or divergence of the laser-Compton beam at and around the focus.

43. The apparatus of concepts 33-42 and 44-56, wherein said opening comprises a diameter that is of the order of the x-ray or gamma-ray focal spot at said opening.

44. The apparatus of concepts 33-43 and 45-56, wherein said aperture is constructed from highly attenuating materials and is configured to have sufficient thickness so as to block any x-rays or gamma rays not passing through said opening.

45. The apparatus of concepts 33-44 and 46-56, wherein said detector comprises a 2-dimensional, x-ray detector system.

46. The apparatus of concepts 33-45 and 47-56, further comprising means for tuning said output beam to just above a specific inner-shell, ionization threshold of a particular atomic species within said object to enhance contrast in the image and/or enable elemental material identification within the object.

47. The apparatus of concepts 33-46 and 48-56, further comprising means for tuning said output beam to a nuclear resonance fluorescence transition of a particular atomic species within said object to enhance contrast and/or enable isotopic material identification within said object.

48. The apparatus of concepts 33-47 and 49-56, wherein said detector comprises a gated detector system configured for gating said detector system so that it is on only during the arrival of ballistic image-forming photons of said diverging beam, thereby further discriminating against background and scattered radiation.

49. The apparatus of concept 34, wherein said at least one x-ray and/or gamma-ray optic comprises a spatially varying structure such that lower energy, higher angle, laser-Compton photons of said output beam that are incident upon said at least one x-ray and/or gamma-ray optic are focused to the same spot and same spot size as higher energy, on axis, laser-Compton photons of said output beam.

50. The apparatus of concept 34, further comprising means for matching chromatic aberrations of at least one x-ray and/or gamma-ray optic to the spectral-angle dependency of said laser-Compton source.

51. The apparatus of concept 34, wherein said at least one x-ray and/or gamma-ray optic is configured to direct said output beam to a focus at said focal point in only one dimension and allow said output beam to diverge in accordance with the physics of the laser-Compton process in the other dimension and wherein said opening is a slit matching the focal size of said output beam in the focusing dimension.

52. The apparatus of concept 51, further comprising means for tuning said output beam to increase contrast and/or enable material identification within said object.

53. The apparatus of concept 34, wherein said at least one x-ray and/or gamma-ray optic comprises two, one-dimensional, compound x-ray optics oriented at 90 degrees with respect to one another and that focus to different locations, wherein one of these produces a fan beam of one dimension of said output beam and the other produces a line focus of said output beam, wherein a slit is placed at said line focus to reduce background radiation.

54. The apparatus of concept 53, further comprising means for tuning said output beam to increase contrast and/or enable material identification within said object.

55. The apparatus of concept 34, wherein said at least one x-ray and/or gamma-ray optic comprises a first one-dimensional, compound x-ray optic and a second one-dimensional, compound x-ray optic oriented at 90 degrees with respect to said first one-dimensional, compound x-ray optic, wherein said the output beam is collimated in one dimension by said first one-dimensional, compound x-ray optic and then focused in the other dimension by said second one-dimensional x-ray optic, wherein a slit is placed at said focal point to reduce background radiation.

56. The apparatus of concept 55, further comprising means for tuning said output beam to increase contrast and/or enable material identification within said object.

57. A method for producing high-contrast, x-ray and/or gamma-ray radiographic images having minimal contributions from object-dependent background radiation, comprising:

providing a low divergence, quasi-monoenergetic, x-ray or gamma-ray output from a laser-Compton source;

utilizing x-ray and/or gamma-ray optics to produce, from said output, a converging or collimated x-ray or gamma-ray beam;

positioning an object within the path of said beam to produce an output beam;

providing a pinhole with its aperture located at the focal position of said output beam, to produce an apertured beam; and recording an image of said apertured beam.

58. An apparatus for producing high-contrast, x-ray and/or gamma-ray radiographic images having minimal contributions from object-dependent background radiation, comprising:

a laser-Compton source for providing a low divergence, quasi-monoenergetic, x-ray or gamma-ray output;

x-ray and/or gamma-ray optics for producing, from said output, a converging or collimated x-ray or gamma-ray beam;

a pinhole with its aperture located at the focal position of said converging or collimated x-ray or gamma-ray beam to produce an apertured beam; and means for recording an image of said apertured beam.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

I claim:

1. A method, comprising:
providing an x-ray or gamma-ray output beam;
directing said output beam through at least one x-ray and/or gamma-ray optic to produce a converging beam directed toward a focal point;
positioning an object within the path of said output beam or said converging beam to produce an altered beam directed toward the focal point;
providing an element having an opening located at the focal point of said altered beam, wherein at least a portion of said altered beam passes through said opening and said focal point to produce a diverging beam; and
detecting said diverging beam.

2. The method of claim 1, wherein said output beam is a quasi-monoenergetic, x-ray or gamma-ray output beam provided from a laser-Compton source.

3. The method of claim 2, wherein said at least one x-ray and/or gamma-ray optic comprises a spatially varying structure such that relatively lower energy, higher angle, laser-Compton photons of said output beam that are incident upon said at least one x-ray and/or gamma-ray optic are focused to the same spot and same spot size as relatively higher energy, on axis, laser-Compton photons of said output beam.

4. The method of claim 2, wherein chromatic aberrations of at least one x-ray and/or gamma-ray optic are matched to the spectral-angle dependency of said laser-Compton source.

5. The method of claim 2, wherein said at least one x-ray and/or gamma-ray optic directs said output beam to a focus at said focal point in only one dimension and allows said output beam to diverge in accordance with physics of the laser-Compton process in the other dimension and wherein said opening is a slit matching the focal size of said output beam in the focusing dimension.

6. The method of claim 5, further comprising tuning said output beam to increase contrast and/or enable material identification within said object.

7. The method of claim 2, wherein said at least one x-ray and/or gamma-ray optic comprises two, one-dimensional, compound x-ray optics oriented at 90 degrees with respect to one another and that focus to different locations, wherein one of these produces a fan beam of one dimension of said output beam and the other produces a line focus of said output beam, and wherein a slit is placed at said line focus to reduce background radiation.

8. The method of claim 7, further comprising tuning said output beam to increase contrast and/or enable material identification within said object.

9. The method of claim 2, wherein said at least one x-ray and/or gamma-ray optic comprises a first one-dimensional, compound x-ray optic and a second one-dimensional, compound x-ray optic oriented at 90 degrees with respect to said first one-dimensional, compound x-ray optic, wherein said the output beam is collimated in one dimension by said first one-dimensional, compound x-ray optic and then focused in the other dimension by said second one-dimensional x-ray optic, wherein a slit is placed at said focal point to reduce background radiation.

10. The method of claim 9, further comprising tuning said output beam to increase contrast and/or enable material identification within said object.

11. The method of claim 1, wherein said at least one x-ray and/or gamma-ray optic comprises at least one refractive x-ray lens.

12. The method of claim 1, wherein said at least one x-ray and/or gamma-ray optic comprises at least one compound x-ray optic.

13. The method of claim 1, wherein said at least one x-ray and/or gamma-ray optic comprises at least one collimating optic followed by at least one focusing optic, wherein said output beam is first collimated by said at least one collimating optic and then focused by said at least one focusing optic to produce said converging beam.

14. The method of claim 13, wherein said object is positioned between said at least one collimating optic and said at least one focusing optic.

15. The method of claim 1, wherein the step of positioning the object comprises:
positioning the object within the path of said converging beam, wherein said object comprises a feature of interest that is smaller than a transverse dimension of said converging beam such that said converging beam completely covers said feature of interest.

16. The method of claim 1, wherein the step of positioning the object comprises:
positioning the object within the path of said converging beam, wherein said object comprises a feature of interest that is larger than a transverse dimension of said converging beam such that said converging beam does not completely cover said feature of interest.

17. The method of claim 16, further comprising scanning said object relative to the position of said converging beam.

18. The method of claim 17, wherein the step of detecting said diverging beam comprises collecting a plurality of images of said diverging beam during the step of scanning said object.

19. The method of claim 18, wherein said plurality of images altogether provide a complete or substantially complete image of said feature of interest.

20. The method of claim 16, wherein a complete or substantially complete image of said feature of interest is obtained by scanning said object and converging beam relative to each other with the location of said converging beam and the location of said opening fixed with respect to one another.

21. The method of claim 1, wherein said element comprises a material that is attenuating to x-rays or gamma rays.

22. The method of claim 1, wherein said opening comprises a shape selected from the group consisting of a pinhole and a slit.

23. The method of claim 1 wherein said opening comprises a conical hole.

24. The method of claim 23, wherein said conical hole matches the convergence and/or divergence of the output beam at and around the focal point.

25. The method of claim 1, wherein said opening comprises a diameter that is of the order of an x-ray or gamma-ray focal spot at said opening.

26. The method of claim 25, wherein the step of positioning the object comprises producing scattered radiation and/or self-emission from said object, wherein all scattered radiation and/or self-emission from said object that does not pass through said opening is substantially rejected and is not detected.

27. The method of claim 1, wherein said element is constructed from attenuating materials and is configured to have sufficient thickness so as to block or substantially block x-rays or gamma rays not passing through said opening in said element.

28. The method of claim 1, wherein the step of detecting said diverging beam is carried out with a 2-dimensional, x-ray detector system.

29. The method of claim 1, further comprising tuning said output beam to above a specific inner-shell, ionization threshold of a particular atomic species within said object.

30. The method of claim 1, further comprising tuning said output beam to a nuclear resonance fluorescence transition of a particular atomic species within said object.

31. The method of claim 1, wherein the step of detecting said diverging beam is carried out with a gated detector system, the method further comprising gating said detector system so that it is responsive to ballistic image-forming photons of said diverging beam only during the arrival of same at said detector system, thereby further discriminating against background and scattered radiation.

32. The method of claim 1, wherein the step of positioning the object within the path of said output beam or said converging beam comprises:
producing a shadow of the object in the altered beam.

33. The method of claim 1, wherein the at least one x-ray and/or gamma-ray optic is formed lithographically in silicon.

34. The method of claim 1, further including recording said diverging beam.

35. An apparatus, comprising:
a source for providing an x-ray or gamma-ray output beam;
at least one x-ray and/or gamma-ray optic to produce, from said output beam, a converging beam directed toward a focal point, wherein an object positioned within the path of said output beam or said converging beam results in an altered beam directed toward the focal point;
an element having an opening located at the focal point of said altered beam, wherein at least a portion of said altered beam passes through said opening and said focal point to produce a diverging beam; and
a detector positioned for detecting said diverging beam.

36. The apparatus of claim 35, wherein said source is a laser-Compton source and wherein said output beam is a quasi-monoenergetic, x-ray or gamma-ray output beam provided from said laser-Compton source.

37. The apparatus of claim 36, wherein said at least one x-ray and/or gamma-ray optic comprises a spatially varying structure such that relatively lower energy, higher angle, laser-Compton photons of said output beam that are incident upon said at least one x-ray and/or gamma-ray optic are focused to the same spot and same spot size as relatively higher energy, on axis, laser-Compton photons of said output beam.

38. The apparatus of claim 36, further comprising means for matching chromatic aberrations of at least one x-ray and/or gamma-ray optic to the spectral-angle dependency of said laser-Compton source.

39. The apparatus of claim 36, wherein said at least one x-ray and/or gamma-ray optic is configured to direct said output beam to a focus at said focal point in one dimension and allow said output beam to diverge in accordance with physics of the laser-Compton process in another dimension and wherein said opening is a slit matching the focal size of said output beam in the focusing dimension.

40. The apparatus of claim 39, further comprising means for tuning said output beam to increase contrast and/or enable material identification within said object.

41. The apparatus of claim 36, wherein said at least one x-ray and/or gamma-ray optic comprises two, one-dimensional, compound x-ray optics oriented at 90 degrees with respect to one another and that focus to different locations, wherein one of these produces a fan beam of one dimension of said output beam and the other produces a line focus of said output beam, and wherein a slit is placed at said line focus to reduce background radiation.

42. The apparatus of claim 41, further comprising means for tuning said output beam to increase contrast and/or enable material identification within said object.

43. The apparatus of claim 36, wherein said at least one x-ray and/or gamma-ray optic comprises a first one-dimensional, compound x-ray optic and a second one-dimensional, compound x-ray optic oriented at 90 degrees with respect to said first one-dimensional, compound x-ray optic, wherein said the output beam is collimated in one dimension by said first one-dimensional, compound x-ray optic and then focused in the other dimension by said second one-dimensional x-ray optic, and wherein a slit is placed at said focal point to reduce background radiation.

44. The apparatus of claim 43, further comprising means for tuning said output beam to increase contrast and/or enable material identification within said object.

45. The apparatus of claim 35, wherein said at least one x-ray and/or gamma-ray optic comprises at least one refractive x-ray lens.

46. The apparatus of claim 35, wherein said at least one x-ray and/or gamma-ray optic comprises at least one compound x-ray optic.

47. The apparatus of claim 35, wherein said at least one x-ray and/or gamma-ray optic comprises at least one collimating optic followed by at least one focusing optic, wherein said output beam is first collimated by said at least one collimating optic and then focused by said at least one focusing optic to produce said converging beam.

48. The apparatus of claim 35, further comprising means for scanning said object relative to the position of said converging beam.

49. The apparatus of claim 35, wherein said element comprises a material that is attenuating to x-rays or gamma rays.

50. The apparatus of claim 35, wherein said opening comprises a shape selected from the group consisting of a pinhole and a slit.

51. The apparatus of claim 35, wherein said opening comprises a conical hole.

52. The apparatus of claim 51, wherein said conical hole matches the convergence and/or divergence of the output beam at and around the focal point.

53. The apparatus of claim 35, wherein said opening comprises a diameter that is of the order of an x-ray or gamma-ray focal spot at said opening.

54. The apparatus of claim 35, wherein said element is constructed from highly attenuating materials and is configured to have sufficient thickness so as to block any x-rays or gamma rays not passing through said opening.

55. The apparatus of claim 35, wherein said detector comprises a 2-dimensional, x-ray detector system.

56. The apparatus of claim 35, further comprising means for tuning said output beam to above a specific inner-shell, ionization threshold of a particular atomic species within said object to enhance contrast in the image and/or enable elemental material identification within the object.

57. The apparatus of claim 35, further comprising means for tuning said output beam to a nuclear resonance fluorescence transition of a particular atomic species within said object to enhance contrast and/or enable isotopic material identification within said object.

58. The apparatus of claim 35, wherein said detector comprises a gated detector system configured for gating said detector system so that it is responsive only during the arrival of ballistic image-forming photons of said diverging beam, thereby further discriminating against background and scattered radiation.

59. The apparatus of claim 35, wherein a shadow of the object is in the altered beam.

60. The apparatus of claim 35, wherein the at least one x-ray and/or gamma-ray optic is formed from silicon.

\* \* \* \* \*